US00PP11167P

United States Patent [19]

Egger

[11] Patent Number: Plant 11,167

[45] Date of Patent: Dec. 28, 1999

[54] LONGIFLORUM×ASIATIC HYBRID LILY PLANT NAMED 'CEB PAZ'

[75] Inventor: Donald L. Egger, Wilsonville, Oreg.

[73] Assignee: Cebeco Lilies, Inc., Aurora, Oreg.

[21] Appl. No.: 08/918,053

[22] Filed: Aug. 25, 1997

[51] Int. Cl.[6] ..... A01H 5/00

[52] U.S. Cl. ..... Plt./313

[58] Field of Search ..... Plt./87.4, 313–315

[56] References Cited

U.S. PATENT DOCUMENTS

P.P. 9,245 8/1995 Egger ..... Plt./87.4

P.P. 9,249 8/1995 Egger ..... Plt./87.4

P.P. 9,626 8/1996 Egger ..... Plt./87.4

OTHER PUBLICATIONS

UPOV–ROM, 1998/01, GTI Jouve Retrieval Software, Plant Variety Database, citation for 'La Paz'.

*Primary Examiner*—Howard J. Locker

*Attorney, Agent, or Firm*—Klarquist Sparkman Campbell Leigh & Whinston, LLC

[57] ABSTRACT

A new and distinct Lily Hybrid having very early blooming, upright, large, yellow flowers and contrasting dark maroon pollen with strong stems; excellent for cut flower production.

2 Drawing Sheets

BACKGROUND OF THE INVENTION

The present invention relates to a new and distinct cultivar of Lily hybrid referred to commercially as a Longiflorum-Asiatic lily hybrid and with a cultivar name 'Ceb Paz'. This invention was developed by controlled breeding in Aurora, Oreg. The seed parent was *Lilium longiflorum* 'Ace'. The pollen parent was an unknown Asiatic lily as mixed pollen was used.

The Longiflorum-Asiatic cross is relatively new to the trade. This type of cross was originally made to create *Lilium longiflorum* hybrids. Instead, due to the difficulty in crossing back to *L. longiflorum,* the plants that were developed were crossed with Asiatic lilies. As such, the results look more like Asiatic lilies. The resulting hybrids typically have several advantages over an Asiatic lily: 1) often larger flowers; 2) often larger, waxier leaves; 3) hybrid vigor; 4) lower susceptibility to scorch; 5) excellent flower texture and substance; 6) more virus resistance; 7) new and clearer colors; and 8) stronger, sturdier stems.

This invention has not been observed under all possible environmental conditions. The phenotype may vary significantly with variations in environment such as temperature, light intensity and day length, without, however, any variation in genotype.

The following traits have been repeatedly observed and are determined to be the basic characteristics of this invention which in combination distinguish this lily as a new and distinct cultivar: 1) large, upright, glowing, solid yellow flowers; 2) large, yellow buds; 3) contrasting dark maroon pollen; 4) tall, vigorous strong stems for cut flowers; and 5) very early bloom time. Bulbs of this plant may be precooled and forced out of season for very uniform cut flower production.

Of the many cultivars known to the inventor, the only other Longiflorum-Asiatic lily hybrids that are similar are varieties owned by Cebeco Lilies, Inc.: 'Ceb Glow' (U.S. Plant Pat. No. 9,245), 'Ceb Sun' (U.S. Plant Pat. No. 9,249), and 'Ceb Dazzle' (U.S. Plant Pat. No. 9,626). Compared to these varieties, 'Ceb Paz' blooms 10 to 20 days earlier, has stronger stems, better bud color, and higher bud count from bulbs of 10 to 14 cm. in circumference.

Asexual reproduction of this new variety has been accomplished at Cebeco Lilies, Inc., Aurora, Oreg. by scaling and tissue culture. The resulting plants have shown that the above-mentioned unique features are stable and reproduce true to type in each successive propagation.

Figure 1:
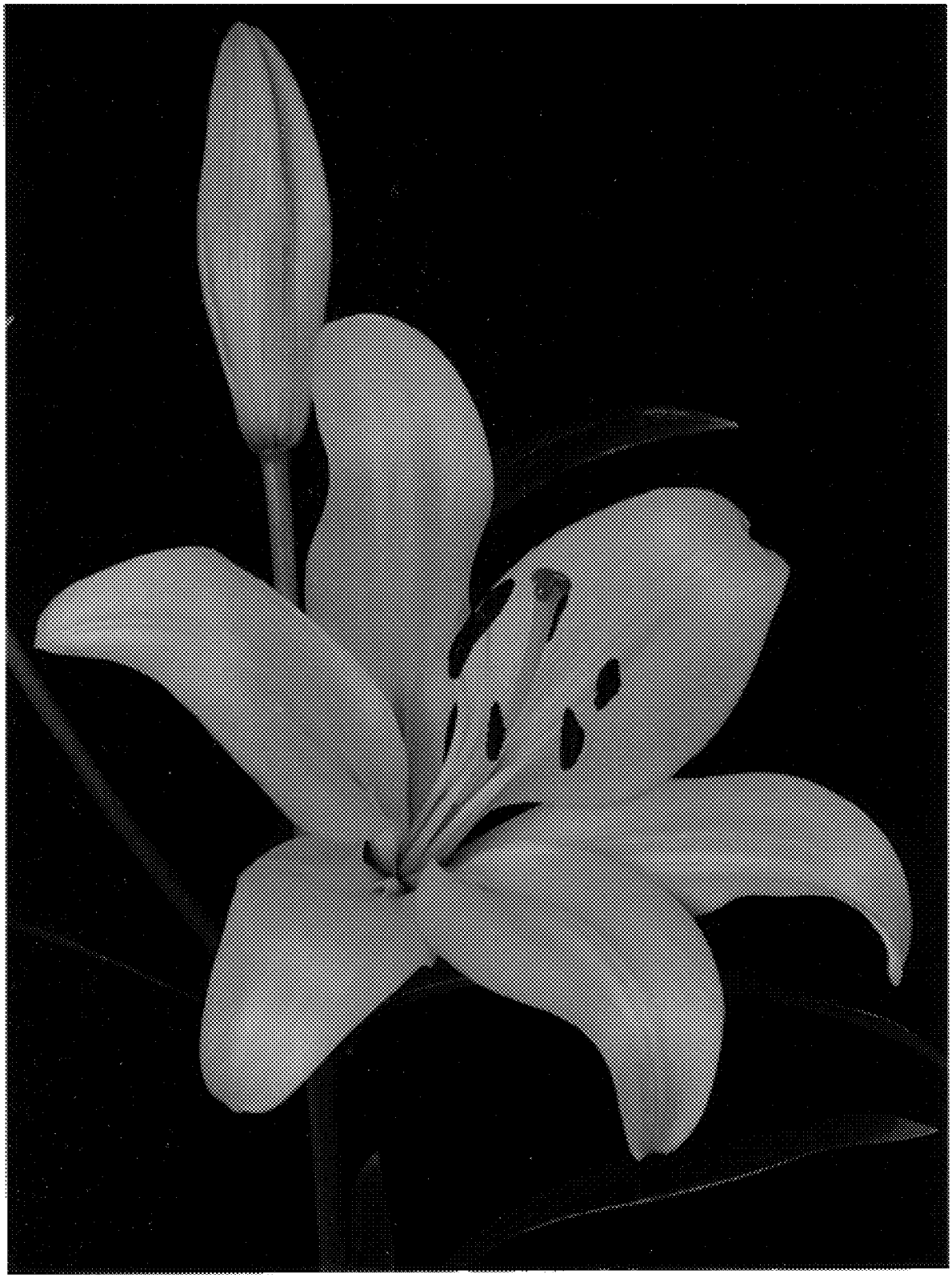
FIG. 1 is a close-up photograph which illustrates a single flower of the new plant.
Figure 2:
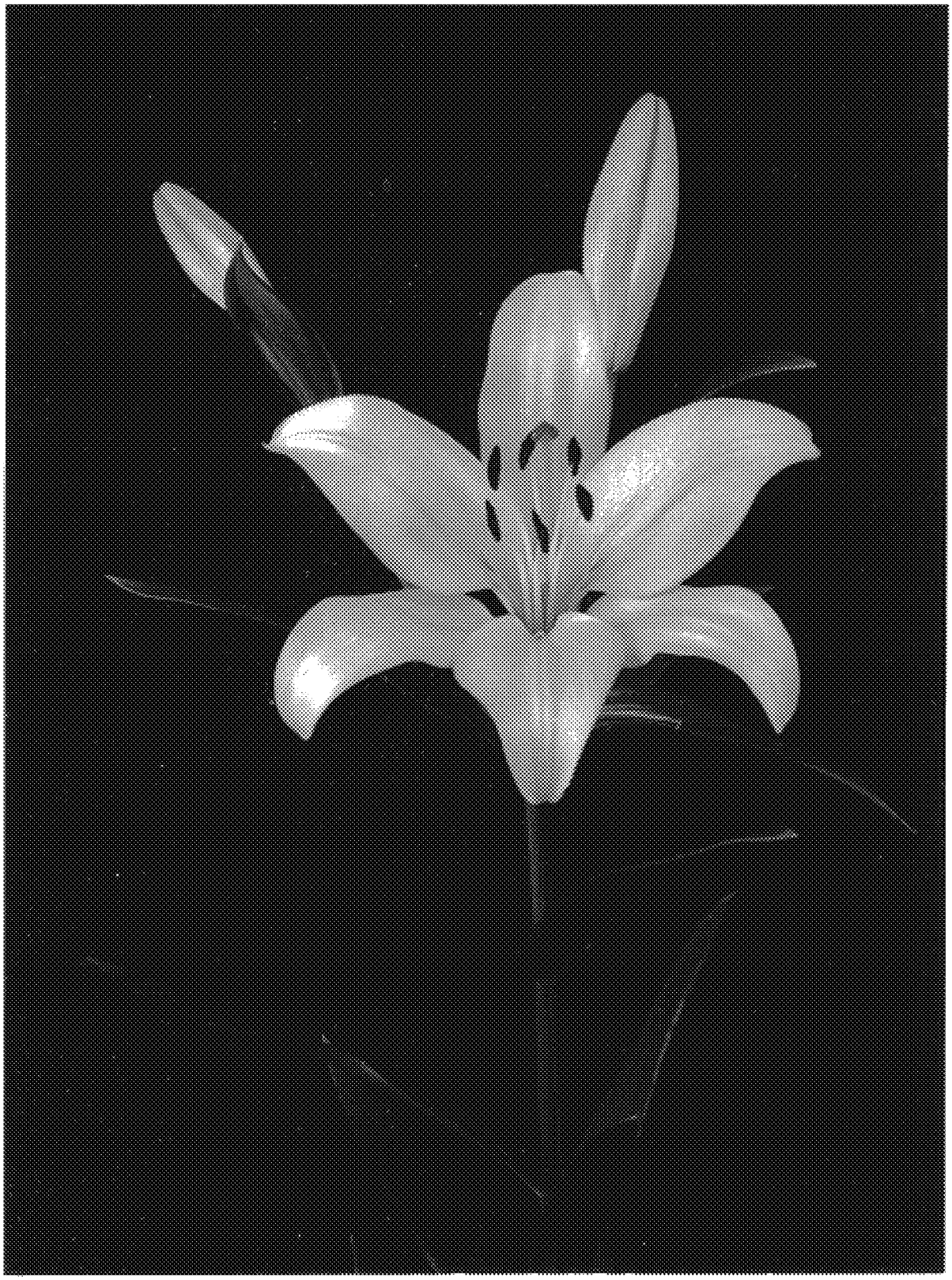
FIG. 2 is a photograph showing the 'Ceb Paz' lily.

The photographs of the drawing were taken in January 1996 in a studio and illustrate the typical flower and foliage form, with color as true as reasonably possible in this type of color photograph.

DETAILED DESCRIPTION

The following is a detailed description of the invention based on plants produced under commercial practices in the Cebeco Lilies, Inc. greenhouses in Aurora, Oreg. in June 1994. Color references are made to The Royal Horticultural Society Colour Chart, except where the context indicates a term having its ordinary dictionary meaning.

THE PLANT

Origin: Seedling.

Parentage:

*Seed parent.*—'Ace'.

*Pollen parent.*—Unknown.

Commercial classification: Upright Longiflorum-Asiatic Hybrid lily, cut flower type.

Classification: Division VIII, according to the Horticultural Classification of Lilies by The Royal Horticultural Society of London.

Form: Single erect stem bearing terminal cluster of flowers.

Height: About 94 cm. from the top of the soil to the top of the flowers from bulbs of 12–14 cm. in circumference.

Growth habit: Vigorous, upright, rigid and strong.

Stem color: Yellow green 144A.

Foliage:

*Arrangement.*—Spiral.

*Quantity.*—Less than average, with internodes of 2.5 to 4.5 cm. long.

*Leaf size.*—Somewhat short; to about 11 cm. long and about 3 cm. wide.
*Leaf shape.*—Lanceolate to ovate lanceolate.
*Texture.*—Leathery.
*Aspect.*—Glossy.
*Color.*—Medium green on both sides, closest to 147A.

Bulbs:
*Size.*—Variable, ranging to about 12 to 14 cm. in circumference as used commercially.
*Color.*—White.

THE BUD

Size: Large. To about 10 cm. long and 3.6 cm. wide just prior to opening.
Shape: Ovoid.
Rate of opening: The mature bud opens slowly in response to light.
Color: Yellow. Yellow Group 7B.

THE FLOWER

Blooming habit: Annually, once and very early season.
Days to bloom: Flowers approximately 65 days after spring greenhouse planting under typical commercial flower forcing conditions of 15 degrees Celsius night time temperatures.
Inflorescence size: About 27 cm. high and 30 cm. wide when there are nine flowers present.
Flower size: Large.
*Diameter.*—About 20 cm.
*Depth.*—About 8 cm.
Borne: In an umbel-like modified raceme of 5 to 10 flowers from bulbs 12 to 14 cm. in circumference.
Shape: When the flower first opens it is bowl shaped. Later the shape flattens out and the tepals reflex slightly at the tips.
Tepalage:
*Number.*—Six.
*Arrangement.*—Imbricated.
*Shape.*—Ovate.
*Margins.*—Slightly undulating on outer tepals.
*Texture.*—Smooth, spongy, waxy.
*Aspect.*—Satiny.
*Size.*—Length: About 11.5 cm. Width: Inner tepals — about 5 cm. Outer tepals — about 4.5 cm. Depth of Imbrication: About 17 mm.
*Nectary.*—About 3 cm. long; yellow green; pubescent; channels apart.
*Projections.*—None.
*Spots.*—None, but the margin on either side of the nectary may have a few dots of red purple.
*Blush.*—On older flowers the blush stays dark, Yellow Group 7A.
*Color.*—A clear, bright yellow with no spots and very little green at the base. Topside: Yellow. Yellow Group 7A, lightening to Yellow Group 8B with age. Topside base: Creamy white. Yellow Group 8D with yellow green along nectary. Bottomside: Yellow. Yellow Group 7A on edges. Yellow Group 4C on rest.
*Discoloration.*—Slightly lighter color with a darker blush.
*Fragrance.*—Slight.
*Lasting quality.*—Good vase life of individual flowers observed to be about eight days.

Pedicel:
*Length.*—Varies from about 5 to 17 cm.
*Color.*—Yellow green 144A.
*Orientation.*—Ascending upwardly from about 5 degrees to 45 degrees from the horizontal.

THE REPRODUCTIVE ORGANS

Stamens:
*Number.*—Six, typical of the genus Lilium.
*Anthers before dehiscence.*—Size: About 24 mm. Color: Multicolored, mostly orange brown. Greyed-Orange 165C and 176C, and Green 137B.
*Filaments.*—Length: About 75 mm. Color: Yellow. Yellow Group 6D at top lightening to creamy white at the base.
*Pollen.*—Color: Dark maroon, Greyed-Purple 187A.

Pistil:
*Number.*—One.
*Style.*—Length: About 7 mm. Color: Yellow at top, Yellow Group 2B to creamy yellow, Yellow Group 11B at base.
*Stigma.*—Color: Purple brown, Greyed-Purple 183A.

THE FRUIT

Fertility: Low.
Shape: Ovoid.
Color at maturity: Soft Brown.

I claim:

1. A new and distinct cultivar of Longiflorum-Asiatic hybrid lily plant substantially as herein shown and described.

* * * * *